(12) United States Patent
Hargett, Jr.

(10) Patent No.: US 6,863,871 B2
(45) Date of Patent: Mar. 8, 2005

(54) SEALING CLOSURE FOR HIGH PRESSURE VESSELS IN MICROWAVE ASSISTED CHEMISTRY

(75) Inventor: Wyatt Price Hargett, Jr., Matthews, NC (US)

(73) Assignee: CEM Corporation, Matthews, NC (US)

( * ) Notice: Subject to any disclaimer, the term of this patent is extended or adjusted under 35 U.S.C. 154(b) by 566 days.

(21) Appl. No.: 09/858,614

(22) Filed: May 16, 2001

(65) Prior Publication Data

US 2001/0022949 A1 Sep. 20, 2001

Related U.S. Application Data

(63) Continuation of application No. 09/323,198, filed on Jun. 1, 1999, now Pat. No. 6,287,526.

(51) Int. Cl.[7] .................................................. B01J 3/00
(52) U.S. Cl. ...................... 422/242; 422/112; 422/113; 422/117; 422/118; 422/198; 422/208
(58) Field of Search ........................... 422/242, 99, 102, 422/104, 112, 113, 117, 118, 198, 208

(56) References Cited

U.S. PATENT DOCUMENTS

| | | |
|---|---|---|
| 4,613,738 A | 9/1986 | Saville |
| 4,882,128 A | 11/1989 | Hukvari et al. |
| 4,904,450 A | 2/1990 | Floyd |
| 4,933,529 A | 6/1990 | Saville |
| 5,230,865 A | 7/1993 | Hargett et al. |
| 5,264,185 A | 11/1993 | Floyd |
| 5,270,010 A | 12/1993 | Lautenschlager |
| 5,320,804 A | 6/1994 | Zakaria et al. |
| 5,368,820 A | 11/1994 | Lautenschlager |
| 5,369,034 A | 11/1994 | Hargett et al. |
| 5,427,741 A | 6/1995 | Bennett |
| 5,520,886 A | 5/1996 | Bennett et al. |
| 6,136,276 A | 10/2000 | Hargett et al. |

FOREIGN PATENT DOCUMENTS

| | | |
|---|---|---|
| DE | G 93 09 355.1 | 12/1994 |
| EP | 0 335 020 A1 | 4/1989 |
| GB | 2184040 A | 6/1987 |

Primary Examiner—Yelena G. Gakh
(74) Attorney, Agent, or Firm—Summa & Allan, P.A.

(57) ABSTRACT

A dynamic sealing structure for pressure vessels used in microwave assisted chemistry is disclosed. The structure includes a cylindrical vessel liner and a removable liner cap, each formed of a microwave transparent material. The liner has a circular mouth with a lip formed of respective first and second beveled edges, with the first beveled edge forming an interior edge of the circular mouth and the second beveled edge forming an exterior edge of the circular mouth. The cap includes respective interior and exterior faces, with a sleeve depending from the interior face and having a circumference that engages the interior surface of the vessel liner for being urged under pressure against the interior surface of the vessel liner. The interior face of the cap comprising a circular channel outward of the sleeve and having a circumference that engages the lip of the vessel liner, and with the channel comprising two beveled edges that respectively engage both beveled edges of the lip of the liner.

20 Claims, 2 Drawing Sheets

SEALING CLOSURE FOR HIGH PRESSURE VESSELS IN MICROWAVE ASSISTED CHEMISTRY

This is a continuation of Ser. No. 09/323,198 filed Jun. 1, 1999, Now U.S. Pat. No. 6,287,526.

FIELD OF THE INVENTION

The present invention relates to methods and apparatus for microwave assisted chemistry, and in particular relates to a closure for a vessel for high pressure applications.

BACKGROUND OF THE INVENTION

Microwave assisted chemistry is the term used to describe systems, apparatus, and methods in which electromagnetic radiation in the microwave frequency range is used to initiate, drive, or otherwise enhance chemical or physical reactions. Microwave assisted chemistry is particularly useful in heating materials that are responsive to microwave radiation because under most circumstances, the resulting heating takes place much more rapidly than it would if the reactions were initiated or accelerated using more conventional heating techniques such as convection or conduction heating.

Microwave assisted chemistry can be used in a variety of chemical processes including moisture determination, ashing, digestion, extraction, and others. Under some circumstances, these various techniques are preferably or necessarily carried out in sealed vessels which, because of the generation or expansion of gases inside, must be able to withstand high pressures.

As well understood by those familiar with the electromagnetic spectrum, the term "microwave" is often used generically to refer to radiation with wavelengths of between about 1000 and 500,000 microns ($\mu$), and corresponding frequencies of between about $1 \times 10^9$ and $5 \times 10^{11}$ Hertz (Hz). These are arbitrary boundaries, however, and other sources refer to microwaves as having frequencies of between about $10^8$ Hz and $10^{12}$ Hz and wavelengths of between about 300 centimeters (cm) and 0.3 millimeters (mm). For commercial and consumer purposes in the United States, the available microwave frequencies are regulated by the Federal Communications Commission and are generally limited to certain frequencies such as 2450 megahertz (MHz). Because of the relatively long wavelength of microwave radiation, microwave assisted chemistry techniques are often carried out in closed vessels which are in turn placed inside a device that bears a superficial relation to a consumer microwave oven, but that is much more sophisticated in its source, waveguide, cavity, and control elements.

This application is also related to co-pending application Ser. No. 09/260,209 filed Mar. 1, 1999 for "Composite Sleeve For Pressure Vessels With Continuously Wound Fabric Reinforcement," the contents of which are incorporated entirely herein by reference. Other patents and pending applications that are illustrative of the types of reaction vessels to which the present invention can apply include U.S. Pat. Nos. 5,427,741 and 5,520,886, both of which are commonly assigned with the present invention. Another version is set forth in co-pending and commonly assigned application Ser. No. 09/062,858, filed Apr. 20, 1998, the contents of which are incorporated entirely herein by reference ("the '858 application").

The composite sleeve set forth in the '209 application has provided, along with its predecessors, the opportunity to greatly increase the reaction pressures at which microwave assisted chemistry can be carried out, while avoiding some of the disadvantages of earlier generations of reaction vessels. In particular, the enhanced performance and controlled, non-shattering failure characteristics of the composite vessels set forth in the '209 application and those related to it, have permitted microwave assisted chemistry to be carried out at pressures as high as 800 pounds per square inch (psi) in the reaction vessel. As set forth in the '209 application and its predecessors, higher pressures can be accommodated to a certain extent by surrounding the reaction vessel with both the composite sleeve and a frame which holds the vessel in place and which urges the vessel lid or cap tightly against the reaction vessel.

As work has progressed at these higher pressures, however, a newer problem has tended to occur. Specifically, because typical reaction vessels are formed of polymers (i.e., transparent to microwaves and resistant to chemical attack) they tend to distort under the extremely high pressures now being used. Furthermore, because the frame keeps the dimensions of the vessel somewhat restricted along the axial direction of the vessel, the distortion that occurs at high pressures tends to be seen as a radial distortion of the typically cylindrical reaction vessels. This radial distortion in turn tends to unseat the vessel lid or cap from the vessel leading to loss of the desired pressures, or of the reagents inside the vessel, or both. In some systems (e.g., the '858 application), the distortion is welcomed as a technique for self-release of high pressures. In other circumstances, however, the high pressure is desired and the vessel should remain closed. Stated differently, the success in developing vessels and systems that can operate at high pressures has raised new issues that must be addressed as the vessels distort under the high pressures.

Accordingly, a need exists for microwave transparent, chemically resistant reaction vessels, typically formed of polymers, that can take advantage of the composite sleeve and frame structure described in the '209 application and its predecessors, and yet which can also withstand the high radial pressures exerted from the interior of the vessel as the reactions proceed, and as the frame maintains the longitudinal dimensions of the vessel and cap relatively the same as they are before reaction occurs. Those familiar with microwave assisted chemistry, and in particular with the types of devices described in the '209 application and its predecessors, will recognize, of course, that the vessel and frame together distort somewhat in a longitudinal direction, but no more than is desired under the design parameters of the vessel and frame. As set forth in the '209 and '858 applications, the slight flexing of the frame, which in turn allows the cap to release slightly, can be desirable under some circumstances as a self-moderating method of controlling the pressure inside the reaction vessel. Such is fine when a certain self release is desired at a particular pressure, but is disadvantageous when the vessel must remain closed at higher pressures in order to encourage a reaction to proceed or to become completed.

Accordingly, a need exists for polymeric reaction vessels and caps that will remain sealed even as internal pressures inside the vessels urge them to distort.

OBJECT AND SUMMARY OF THE INVENTION

Therefore, it is an object of the present invention to provide reaction vessels that will remain sealed even as high pressures inside the vessels urge them to distort, and while such distortion is taking place.

The invention meets this object with a dynamic sealing structure for pressure vessels used in microwave assisted chemistry. The structure comprises a vessel and a cap for the vessel. First means on the cap urge portions of the cap in radial sealing relationship against the interior of the vessel when the contents of the vessel are under pressure. Second means on the cap urge portions of the cap in radial sealing relationship against the exterior of the vessel. More specifically, the reaction vessel is cylindrical, and one end of which defines a circular mouth into which reagents can be placed. The circular cap has respective interior and exterior faces with respect to said vessel, and a sleeve depends from the interior face of the cap and has a diameter sufficient for the sleeve to engage the interior surface of the vessel. The interior face of the cap also has a circular channel having a width sufficient to accept the circular mouth of the reaction vessel with those portions of the cap that are radially exterior to the channel overlapping the exterior of the reaction vessel.

Most preferably, the liner has a circular mouth with a lip formed of respective first and second beveled edges, with the first beveled edge forming an interior edge of the circular mouth and the second beveled edge forming an exterior edge of the circular mouth. The cap comprises respective interior and exterior faces, with a hollow sleeve depending from the interior face and having a circumference that engages the interior surface of the vessel liner for being urged under pressure against the interior surface of the vessel liner. The interior face of the cap also includes a circular channel outward of said sleeve and having a circumference that engages the lip of the vessel liner. The channel comprises two beveled edges that respectively engage both beveled edges of the lip of the liner.

The foregoing and other objects and advantages of the invention and the manner in which the same are accomplished will become clearer based on the following detailed description taken in conjunction with the accompanying drawings in which:

DETAILED DESCRIPTION

Figure 1:
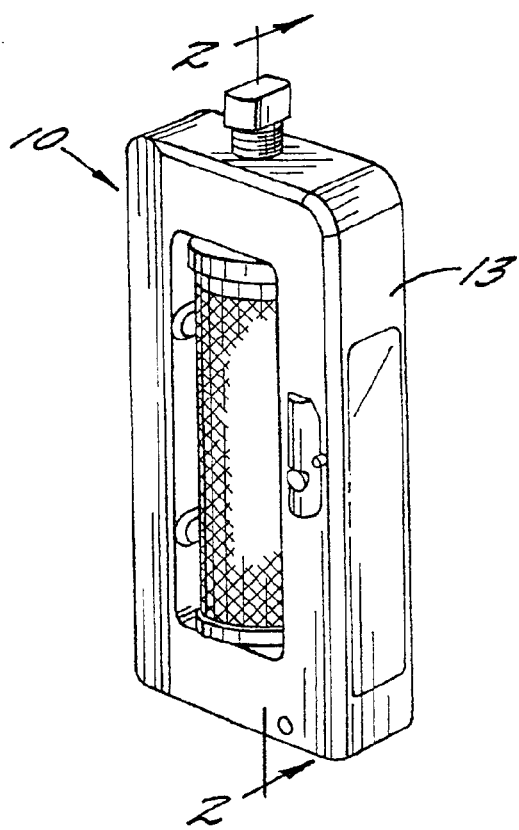
FIG. 1 is a perspective view of a vessel and frame according to the present invention.
Figure 2:
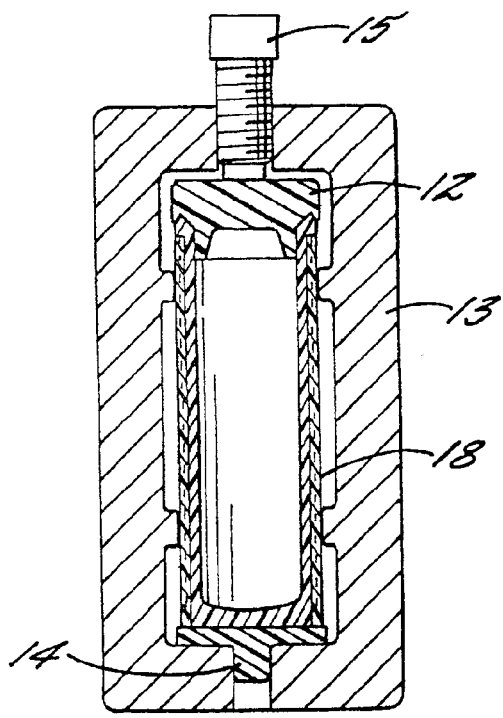
FIG. 2 is a cross sectional view taken along lines 2—2 of FIG. 1 and showing some of the details of the invention.
Figure 3:
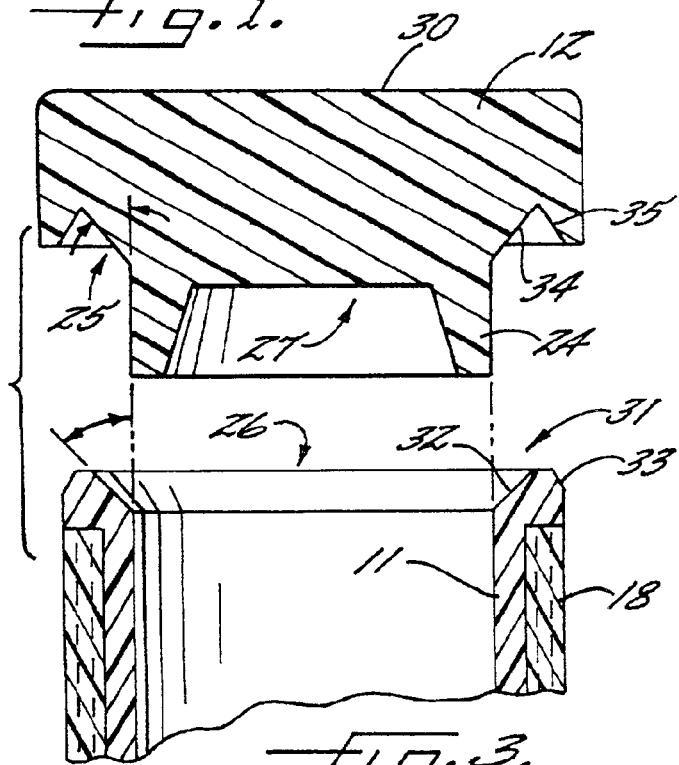
FIG. 3 is an exploded cross sectional view of the upper portions of a reaction vessel and its cap in accordance with the present invention.
Figure 4:
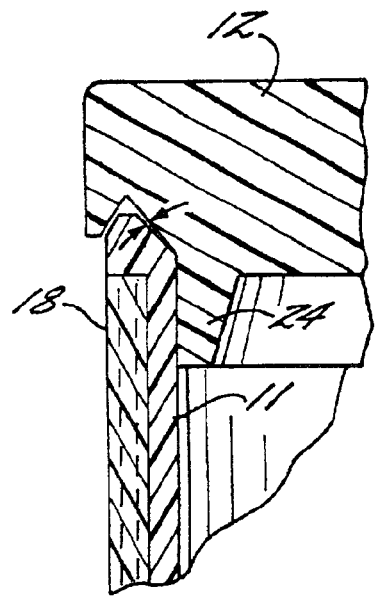
FIG. 4 is a partial cross sectional view similar to FIG. 3, but showing the cap engaged with the reaction vessel.

The present invention is a dynamic sealing structure for pressure vessels used in microwave assisted chemistry. FIGS. 1 and 2 illustrate the overall components of the ceiling structure and the environment in which it is used. The perspective view of FIG. 1 shows a vessel assembly broadly designated at 10. The vessel assembly 10 includes a vessel 11 which is best illustrated in FIGS. 2, 3, and 4. The vessel 11 is preferably cylindrical in shape and formed of a microwave transparent, chemically resistant material such as Teflon®. The vessel includes a cap 12 for closing the vessel and keeping the contents inside. The vessel and cap are surrounded by a frame 13 that helps maintain the cap 12 in place against the vessel the 11. As illustrated in FIGS. 1 and 2, the vessel assembly 10 further includes a mounting plug 14 at lower portions of the frame 13 against which the vessel 11 can rest, along with a tightening bolt 15 that can be used to bring and adjustable amount of pressure (depending upon how tightly the bolt is tightened) against the cap 12. In some embodiments, the vessel can include a load disk (not shown) positioned between the bolt 15 and the cap 12 that helps structurally reinforce the entire vessel and the bolt 15 is tightened.

Figure 5:
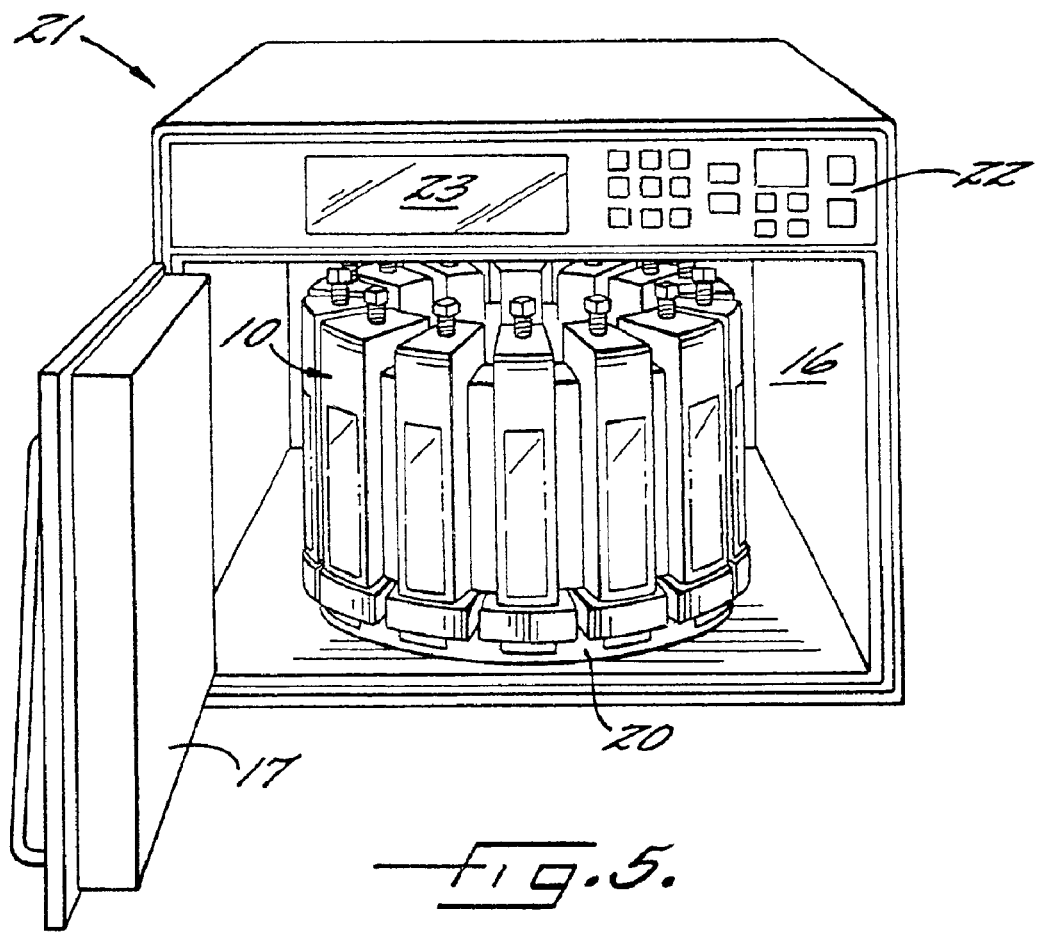
FIG. 5 is a front perspective view of a microwave system according to the present invention showing a plurality of vessels and frames according to the invention in the cavity of a microwave device suitable for microwave assisted chemistry.

FIG. 5 illustrates a typical manner in which a plurality of the vessel systems are placed into the cavity of a microwave system that includes a source of microwave radiation. Apart from the closure of the present invention, the structure and operation of devices such as those illustrated in FIG. 5 are generally well understood in this art and will not be otherwise explained in detail. In general, the cavity 16 has a door 17 that allows easy access to the plurality of vessels systems 10 that are positioned therein. The vessel systems are preferably mounted on a turntable 20 so that they can be moved while microwaves are being applied. As known to those familiar with microwaves, such movement helps make sure that the contents of each of the vessels are exposed to substantially the same amount of microwave radiation at the same time. The overall device in FIG. 5 is designated at 21 and includes a microwave source, a control system symbolized by the control panel 22 and a display 23 that provides appropriate information about the operation of the device, and potentially information about the conditions inside of the reaction vessels. As in other versions of this type of device 21, one of the vessel systems 10 typically is set up to receive some sort of temperature measuring and pressure measuring device that can be monitored by the operator, or monitored automatically by the device 21, as the reactions proceed.

In the illustrated embodiments, the vessel system 10 further includes a composite sleeve 18 of the type that is described in the above-incorporated '209 application and its predecessors. As in the case of all the other materials, the composite sleeve is likewise formed of a material that is substantially transparent to electromagnetic radiation within the microwave frequency range, and is similarly resistant to attack from most harsh chemicals, particularly mineral acids.

FIGS. 3 and 4 illustrate the particular features of the present invention. In its broadest sense, the invention comprises first means on the cap 12 and shown as the depending sleeve 24 for urging portions of the cap 12 in radial (as opposed to axial) sealing relationship against the interior of the vessel 11, when the contents of the vessel 11 are under pressure. The invention further comprises a second means on the cap, and illustrated as the circular channel 25 in the cap 12, for urging portions of the cap 12 in radial sealing relationship against the exterior of the vessel 11, when the contents of the vessel 11 are under pressure. Stated differently, the dynamic sealing structure provides a force against the interior of the vessel that engages the cap 12 to the interior of the vessel 11, while at the same time urging the cap 12 against the exterior of the vessel.

The dynamic sealing structure, according to the present invention can be further understood as being formed of the cylindrical reaction vessel 11, one end of which defines a circular mouth indicated broadly in the drawings at 26. The mouth 26 is, of course, the position at which reagents can be placed into the vessel 11. In some circumstances, the vessel 11 is also referred to as the "liner," because it forms the inside lining of the overall vessel system 10.

The circular cap 12 for the vessel 11 has respective interior and exterior faces 27 and 30. In this embodiment, the hollow sleeve 24 depends from the interior face 27 of the cap 12 and has a diameter sufficient for the sleeve 24 to engage the interior surface of the vessel 11.

The cap 12 also includes the circular channel 25 in its interior face 27. The circular channel 25 has a width sufficient to accept the circular mouth 26 of the reaction vessel 11 with those portions of the Cap 12 that are radially exterior to the channel 25 overlapping the exterior of the reaction vessel 11.

As set forth earlier, one of the potential problems with previous combinations of vessels and caps was the tendency of the vessel to distort under pressure, and particularly to distort radially given that its axial (i.e., longitudinal) expansion is limited or controlled by the frame 13 and the bolt 15. As a result, the radial distortion of the vessel 11 would tend to break the seal between the vessel 11 and the cap 12. In the invention, however, and as best illustrated in FIGS. 3 and 4, the hollow sleeve 24 provides a mechanism by which increased pressure within the vessel 11 urges the sleeve 24 tightly against the inner surface of the vessel 11, thus providing an interior seal against the distortion forces. The channel 25 and the overlapping portions of the cap 12 compliment the action of the sleeve by providing a surface against which the radially distorted vessel 11 will bear and yet without losing its seal.

Stated differently, high pressure in the vessel 11 urges the sleeve 24 tightly against the interior of the vessel 11, and also urges the vessel 11 tightly against the channel 25 in the cap 12.

In the preferred embodiment, and as illustrated in FIGS. 3 and 4, the circular channel 25 has an oblique cross section formed at an acute angle. Other possibilities exist for the channel cross-section, however, and it will be understood that these likewise form part of the claimed invention. For example, the circular channel 25 could have a rectangular cross section, a curvilinear cross section, or even a combination of these geometric features. The oblique cross section described herein, however, tends to take up the least amount of space and thus provides for a more efficiently sized vessel system. Similarly, the vessel system could include a channel in the liner mouth and a beveled lip in the cap 12. Such an arrangement would be less conducive to liquid handling, however, because of the greater possibility that reaction liquids could spill into the channel while filling and emptying the vessel, and the arrangement could also tend to be bulkier than the preferred embodiment.

Turning to FIGS. 3 and 4 in even greater detail, these illustrate the cylindrical vessel liner 11 and the removable cap 12 with the vessel 11 having a circular mouth 26 with a lip broadly designated at 31 that is formed of respective first and second beveled edges 32 and 33. The first beveled edge 32 forms the interior edge of the circular mouth 26, while the second beveled edge 33 forms the exterior edge of the circular mouth 26.

As just described, the cap 12 includes the respective interior and exterior faces 27 and 30, with the hollow sleeve 24 depending from the interior face 27. The sleeve 24 has a circumference that engages the inner surface of the vessel liner 11 for being urged under pressure against the interior of the vessel liner 11.

In this embodiment, the interior face 27 of the cap includes a circular channel outward of the sleeve 24 and having a circumference that engages the lip 31 of the vessel 11. In a manner complimentary of the lip 31, the channel 25 comprises two beveled edges 34 and 35 that respectively engage both beveled edges 32 and 33 of the lip 31 of the liner 11. As noted above, the use of the beveled lip 31 and beveled channel 25 is the most efficient for combining both the sealing properties of the system with the most efficient use of space.

FIG. 4 illustrates that in preferred embodiments, the bevel 34 of the channel 25 is not formed at exactly the same angle as the bevel 32 on the lip 31 of the vessel 11. Instead, the bevels 32 and 34 form a slight angle with respect to each other that enhances the dynamic nature of the seal as pressure distorts the vessel 11. By keeping the bevel 34 at a slightly different angle from the bevel 32, the structure ensures that there is always some contact between the surface of bevel 34 and the surface of bevel 32 even when the pieces distort under pressure or when they are not machined perfectly during manufacture. Stated differently, when the bevels have the same angle, they require higher design tolerances and they are somewhat less likely (although not necessarily) to remain in perfect contact under high pressures. Satisfying both of these under all conditions is somewhat difficult, although not impossible. With the angles being slightly different, however, the point of contact between surface 34 and surface 32 can in effect migrate as the vessel 11 distorts, and yet while keeping the surfaces 32 and 34 in contact with each other at all times. The difference in angle also forms a structure in which the surfaces 34 and 32 are more likely to meet at a point (i.e., a circumferential line) rather than across a strip of each. Because the surfaces 34 and 32 meet at a point, the unit load at that point is always relatively high; i.e. producing a more effective seal.

The angle between the bevel surface 32 of the lip 31 and the bevel surface 34 of the channel 25 should be large enough to permit this dynamic sealing, but less than an angle that would require too much force to keep the cap 12 sealed on the liner 11 under most conditions. Thus, it presently appears that an angle of at least about two degrees is required, but that an angle of about eight degrees is too large. Accordingly, in presently preferred embodiments, the angle between the surface 32 of the lip 31 and the surface 34 of the channel 25 is maintained at about four degrees.

As in all of the embodiments described herein, the cap and liner of this embodiment are preferably used in conjunction with the composite reinforcing sleeve 18, the surrounding frame 13, and the tightening bolt 15. All of these are made of materials that are substantially transparent to microwave radiation, are resistant to chemical attack, and which meet the structural strength requirements of the reactions intended to be carried out therein. Different materials, or strengths of materials, can be designed or selected for different applications for reasons of efficient and economical use of materials. Stated differently, it will be understood that several different type of materials can be used for each of the elements described herein depending upon the conditions of expected use, but the particular types of polymers or other materials used does not limit the scope of the present invention. Instead, the scope of the present invention is such that the invention can be advantageously used with a number of such different materials.

As in the previous embodiments, the embodiment with the beveled edges can be incorporated with a plurality of other such embodiments in a microwave device such as the one illustrated at 21 for carrying out a plurality of chemical reactions at the same time in the single cavity 16.

As a further detail, the frame is typically selected from the group consisting of high-strength thermoplastic polymers and engineering polymers. Typical polymers include, but are not limited to, ABS resins, acrylic resins, nylon, PEEK resins, phenolformaldehyde resins, polybutylene terephthalate, polycarbonate, higher strength polyethylene, polypropylene, and polystyrene, polyvinylchloride (PVC), and urea formaldehyde resins. Particularly preferred plastics are the polyether imide plastics such as ULTEM™ from General Electric. Thermoplastic materials can be made with varying strengths by a number of polymerization and catalyzation techniques that are well understood by those in the polymer arts and will not be otherwise repeated herein Those familiar with polymers that are microwave transparent, chemically inert, and structurally appropriate will recognize that other polymers meeting these characteristics can be used for the vessel and cap and can be selected without undue experimentation. Exemplary fluoropolymers and other materials are also described in U.S. Pat. No. 5,520,886, at column 5, lines 17–55. The contents of U.S. Pat. No. 5,520,886 are incorporated entirely herein by reference.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A dynamic sealing structure for pressure vessels used in microwave assisted chemistry, and comprising:
   a cylindrical vessel; and a cylindrical cap for said vessel;
   first means on said cylindrical cap for urging portions of said cap radially outwardly in sealing relationship against the cylindrical interior of said cylindrical vessel when the contents of said vessel are under pressure; and
   second means on said cap for being urged against in radial sealing relationship by the exterior of said vessel when said vessel expands when the contents of said vessel are under pressure so that said first and second means maintain said cap and said vessel in sealing relationship as high pressures inside said vessel urge said vessel and said cap to distort.

2. A dynamic sealing structure according to claim 1 and further comprising third means on the exterior of said vessel for engaging said second means on said cap when the contents of said vessel are under pressure.

3. A dynamic sealing structure according to claim 2 and further comprising a frame surrounding said vessel and said cap and bearing against said vessel and said cap.

4. A dynamic sealing structure according to claim 3 wherein said vessel, said cap and said frame are all formed of materials that are transparent to microwave radiation and resistant to chemical attack.

5. A dynamic sealing structure according to claim 4 and further comprising a composite sleeve surrounding said vessel.

6. A system for microwave assisted chemistry comprising:
   a microwave source;
   a cavity in microwave communication with said source; and
   a plurality of vessels according to claim 5 in said cavity for being exposed to microwaves generated by said source and propagated into said cavity.

7. A dynamic sealing structure for pressure vessels used in microwave assisted chemistry, and comprising:
   a cylindrical reaction vessel, one end of which defines a circular mouth into which reagents can be placed; and
   a circular cap for said vessel, said cap having respective interior and exterior faces with respect to said vessel;
   a sleeve depending from said interior face of said cap and having a diameter sufficient for said sleeve to engage the interior surface of said vessel; and
   a circular channel in said interior face of said cap having a width sufficient to accept said circular mouth of said reaction vessel with those portions of said cap radially exterior to said channel overlapping the exterior of said reaction vessel, thereby urging portions of said cap to remain in radial sealing relationship against the exterior of said vessel when the contents of said vessel are under pressure to thereby maintain a sealing relationship between said cap and said vessel as high pressure inside said vessel urge said vessel and said cap to distort.

8. A dynamic sealing structure according to claim 7 wherein said circular channel has a rectangular cross section.

9. A dynamic sealing structure according to claim 7 wherein said circular channel has an oblique cross section.

10. A dynamic sealing structure according to claim 7 wherein said circular channel has a curvilinear cross section.

11. A dynamic sealing structure according to claim 7 and further comprising:
    a rectangular frame surrounding said vessel and said cap; and
    a bolt threaded into said frame coaxial with said vessel and against said cap for being adjustably tightened to bear against said vessel said cap.

12. A dynamic sealing structure according to claim 11 wherein said vessel, said cap said frame and said bolt are all formed of materials that are transparent to microwave radiation and resistant to chemical attack.

13. A dynamic sealing structure according to claim 12 and further comprising a composite sleeve surrounding said vessel.

14. A system for microwave assisted chemistry comprising:
    a microwave source;
    a cavity in microwave communication with said source; and
    a plurality of vessels according to claim 13 in said cavity for being exposed to microwaves generated by said source and propagated into said cavity.

15. A dynamic sealing structure for pressure vessels used in microwave assisted chemistry, and comprising:
    a cylindrical vessel liner and a removable liner cap, each formed of a microwave transparent material;
    said liner having a circular mouth with a lip formed of respective first and second beveled edges
    said first beveled edge forming an interior edge of said circular mouth;
    said second beveled edge forming an exterior edge of said circular mouth;
    said cap comprising respective interior and exterior faces, with a sleeve depending from said interior face and having a circumference that engages the interior surface of said vessel liner for being urged under pressure against the interior surface of said vessel liner;
    said interior face of said cap comprising a circular channel outward of said sleeve and having a circumference that engages said lip of said vessel liner;
    said channel comprising two beveled edges that respectively engage both beveled edges of said lip of said liner; and
    said exterior face of said cap being in radial sealing relationship against the exterior of said vessel when contents of said vessel are under pressure, to thereby maintain a sealing relationship as high pressures inside said vessel urge said vessel and said cap to distort.

16. A dynamic sealing structure according to claim 15 and further comprising:

a rectangular frame surrounding said vessel and said cap;

a bolt threaded into said frame coaxial with said vessel and against said cap for being adjustably tightened to bear against said vessel said cap;

a composite sleeve surrounding said vessel;

said frame, said bolt and said composite sleeve all being formed of materials that are transparent to microwave radiation and resistant to chemical attack.

17. A system for microwave assisted chemistry comprising:

a microwave source;

a cavity in microwave communication with said source; and a plurality of vessels according to claim 16 in said cavity for being exposed to microwaves generated by said source and propagated into said cavity.

18. A dynamic sealing system according to claim 16 wherein said frame and bolt are formed of a polymeric material selected from the group consisting of: acrylolnitrile-butadiene-styrene resins, acrylic resins, nylon, PEEK resins, phenolformaldehyde resins, polybutylene terephthalate, polycarbonate, polyethylene, polypropylene, polystyrene, polyvinylchloride, and urea formaldehyde resins.

19. A dynamic sealing system according to claim 16 wherein said composite sleeve comprises a plurality of adjacent layers of fabric and polymers.

20. A dynamic sealing structure according to claim 15 wherein said liner and cap are formed of a fluoropolymer.

* * * * *